United States Patent [19]

MacNeil et al.

[11] Patent Number: 5,312,753
[45] Date of Patent: May 17, 1994

[54] STRAIN OF STREPTOMYCES AVERMITILIS CAPABLE OF GLYCOSYLATING AVERMECTIN COMPOUNDS AT THE 13- AND 14A POSITIONS

[75] Inventors: Douglas J. MacNeil; Tanya MacNeil, both of Westfield, N.J.

[73] Assignee: Merck & Co., Inc., Rahway, N.J.

[21] Appl. No.: 855,311

[22] Filed: Mar. 23, 1992

[51] Int. Cl.$^5$ ............................ C12N 1/20; C12N 1/00
[52] U.S. Cl. ................................. 435/253.5; 435/243
[58] Field of Search ............................ 435/243, 253.5

[56] References Cited

U.S. PATENT DOCUMENTS

| | | | |
|---|---|---|---|
| 3,950,360 | 4/1976 | Aoki et al. | 435/119 |
| 4,203,976 | 5/1980 | Fisher et al. | 514/7.1 |
| 4,310,519 | 1/1982 | Albers-Schonberg et al. | 435/119 |

FOREIGN PATENT DOCUMENTS

| | | |
|---|---|---|
| 144285 | 10/1984 | European Pat. Off. . |
| 242052 | 3/1987 | European Pat. Off. . |
| 0341973 | 5/1989 | European Pat. Off. . |

Primary Examiner—Douglas W. Robinson
Assistant Examiner—Maria L. Osoteo
Attorney, Agent, or Firm—David L. Rose; Joseph F. DiPrima

[57] ABSTRACT

Avermectin compounds are glycosylated at the 4',13- or 14a-positions by adding the avermectin compounds to the fermentation medium of a novel strain of *Streptomyces avermitilis*. The 13-hydroxy and 14a-hydroxy methyl groups of the avermectin compound are glycosylated with a glycosyl moiety, specifically an oleandrose group. The new strain offers the added advantage of not producing any C5-O-methylation products. The compounds are potent anthelmintic and antiparasite agents, and compositions for such uses are also disclosed.

2 Claims, No Drawings

STRAIN OF STREPTOMYCES AVERMITILIS CAPABLE OF GLYCOSYLATING AVERMECTIN COMPOUNDS AT THE 13- AND 14A POSITIONS

BACKGROUND

Avermectin compounds are natural products produced by the fermentation of *Streptomyces avermitilis* as disclosed in U.S. Pat. No. 4,310,519 to Albers-Schonberg et al. The avermectin compounds have a natural α-L-oleandrosyl-α-L-oleandrosyloxy group at the 13-position. In U.S. Pat. No. 4,203,976 to Fischer et al certain synthetic procedures are disclosed for glycosylating various hydroxy groups or the avermectin molecule, including the 4″-hydroxy of the avermectin disaccharide group but not the 14a-position.

SUMMARY OF THE INVENTION

This invention is concerned with the preparation of avermectin compounds with a glycosyl group, specifically an oleandrosyl group, substituted at the 13- and 14a-positions of the avermectin compounds which are prepared by fermenting an avermectin aglycone or a 14a-hydroxy avermectin compound in a culture medium of a novel strain of *Streptomyces avermitilis* MA 6941, ATCC 55292. The compounds produced by the fermentation are potent antiparasitic and anthelmintic agents.

DESCRIPTION OF THE INVENTION

This invention is concerned with the preparation of avermectin compounds where an oleandrosyl group is placed at the 4′, 13- and 14a-positions of an avermectin compound. The process is carried out by culturing the microorganism *Streptomyces avermitilis* in a culture medium and adding the avermectin monosaccharide, aglycone or the 14a-hydroxy avermectin starting material to the fermentation broth. The culture *Streptomyces avermitilis* is a new microorganism that has been deposited with the American Type Culture Collection at 12301 Parklawn Dr. Rockville, Md. 20852 under the accession number ATCC 55292. The deposit was made under the Budapest Treaty for the deposit of microorganisms for patent purposes on 55292.

The strain of *Streptomyces avermitilis* MA 6941 is a novel mutant strain that does not produce any avermectin compounds in the absence of any such compounds added to the fermentation broth. The strain glycosylates but does not carry out C5-O-methylation. The strain has had deleted therefrom the gene for C5-O-methyl transferase and a portion of the DNA required for the synthesis of the avermectin aglycone structure.

The morphological characteristics of *Streptomyces avermitilis* MA 6941, ATCC 55292, are as follows:

The following is a general description of *Streptomyces avermitilis* strain MA6941. The culture is used for the glycosylation of avermectin monosaccharides, aglycones or 14a-hydroxy derivatives without accompanying methylation. Observations of growth, general cultural characteristics and carbon source utilization were made in accordance with the methods of Shirling and Gottleib (Internat. J. System. Bacteriol. 16: 313–340). Chemical composition of the cells was determined using the methods of Lechevalier and Lechevalier (in Actinomycete Taxonomy, A. Dietz and D. W. Thayer, Ed. Society for Industrial Microbiology, 1980). Coloration of the culture was determined by comparison with color standards contained in the Inter-Society Color Council-National Bureau of Standards Centroid Color Charts (U.S. Dept. of Commerce National Bureau of Standards supplement to NBS Circular 553, 1985).

Analysis of Cell Wall Composition—Peptidoglycan contains LL-diaminopimelic acid.

General growth characteristics—Good growth on yeast malt extract agar (YME), glycerol asparagine agar, inorganic salt starch agar, oatmeal, trypticase soy agar and peptone iron agar. Poor growth on Czapek's agar and tap water agar supplemented with NZ-amine (Shefield Chemical Co.) Culture also grows in tryptone yeast extract broth. Culture grows at 27° C. and 37° C.

Colony morphology—(on YME at 21 d) Substrate mycelium is light brown. Aerial mycelium white. Spore mass is abundant and light greenish gray in color. Melanoid pigment is produced. Colonies are opaque, raised and have entire edges, rubbery in consistency with a matte surface texture.

Micromorphology—Aerial mycelia (0.57–0.76 μm) arise from substrate mycelia and are branched, short and flexous. In mature cultures (7–28d p.i.) the aerial mycelium terminates in spiral chains of spores that occasionally terminate in knob like structures. This characteristic is especially noticeable in areas of dense aerial development. Sporulation occurs on YME, inorganic salts-starch agar, oatmeal, glycerol asparagine agar, tap water agar with NZ-amine and Czapek's agar.

Miscellaneous physiological reactions—Culture produces $H_2S$ in peptone-iron agar. Melanoid pigments are formed in TY broth, and on YME, trypticase-soy and peptone iron agar slants. Starch is weakly hydrolyzed at 21d but not at 14d p.i.. Carbon source utilization pattern is as follows: good utilization of D-fructose, α-D-glucuse, α-D-lactose, β-D-lactose, D-mannitol, D-mannose, L-rhamnose, D-xylose; moderate utilization of L-arabinose, inositol, D-maltose, D-raffinose; poor utilization of D-arabinose, sucrose.

Tables 1 and 2 summarize the cultural characteristics and carbohydrate utilization of Streptomyces avermitilis MA6941.

Diagnosis—These results compare favorably with the published description of the parent strain *Streptomyces avermitilis*.

TABLE 1

Cultural characteristics of *Streptomyces avermitilis* MA6941 at 21 days

| Medium | Amount of Growth | Aerial Mycelium and/or Spores | Soluble Pigments | Reverse Color |
|---|---|---|---|---|
| Yeast Extract Malt Extract | good | Aerial mycelium light greenish gray (154 l.gGray). Spores borne in extended spiral chains. | brown | Grayish brown (61 gy.Br) |
| Glucose Asparagine | good | Aerial mycelium greenish white (153 gWhite). Spores borne in extended spiral chains. | none noted | Grayish yellow (90 gy.Y) |
| Inorganic Salts Starch | good | Aerial mycelium light greenish gray (154 l.gGray). Spores borne in extended spiral chains. Starch weakly hydrolyzed. | dark gray | Grayish olive green (127 gy.OlG) |

TABLE 1-continued
Cultural characteristics of
*Streptomyces avermitilis* MA6941 at 21 days

| Medium | Amount of Growth | Aerial Mycelium and/or Spores | Soluble Pigments | Reverse Color |
|---|---|---|---|---|
| Oatmeal | good | Aerial mycelium greenish white (153 gWhite). Spores borne in extended spiral chains. | none noted | Grayish yellow (90 gy.Y) |
| Tap Water | sparse | No aerial mass observed. | none noted | Transparent |
| Czapek | sparse | Transparent. Spores borne in extended spiral chains. | none noted | Transparent |
| Peptone Iron | good | | | Melanin positive, $H_2S$ positive. |

TABLE 2
Carbohydrate utilization pattern of
*Streptomyces avermitilis* MA6941 at 21 days

| Carbon source | Utilization |
|---|---|
| D-arabinose | 1 |
| L-arabinose | 2 |
| D-fructose | 3 |
| inositol | 2 |
| α-D-lactose | 3 |
| β-D-lactose | 3 |
| D-maltose | 2 |
| D-mannitol | 3 |
| D-mannose | 3 |
| D-raffinose | 2 |
| L-rhamnose | 3 |
| sucrose | 1 |
| D-xylose | 3 |
| a-D-glucose (control) | 3 |

3 = good utilization
2 = moderate utilization
1 = poor utilization
0 = no utilization The process utilizing the novel microorganism of the instant invention is best realized in the following reaction scheme:

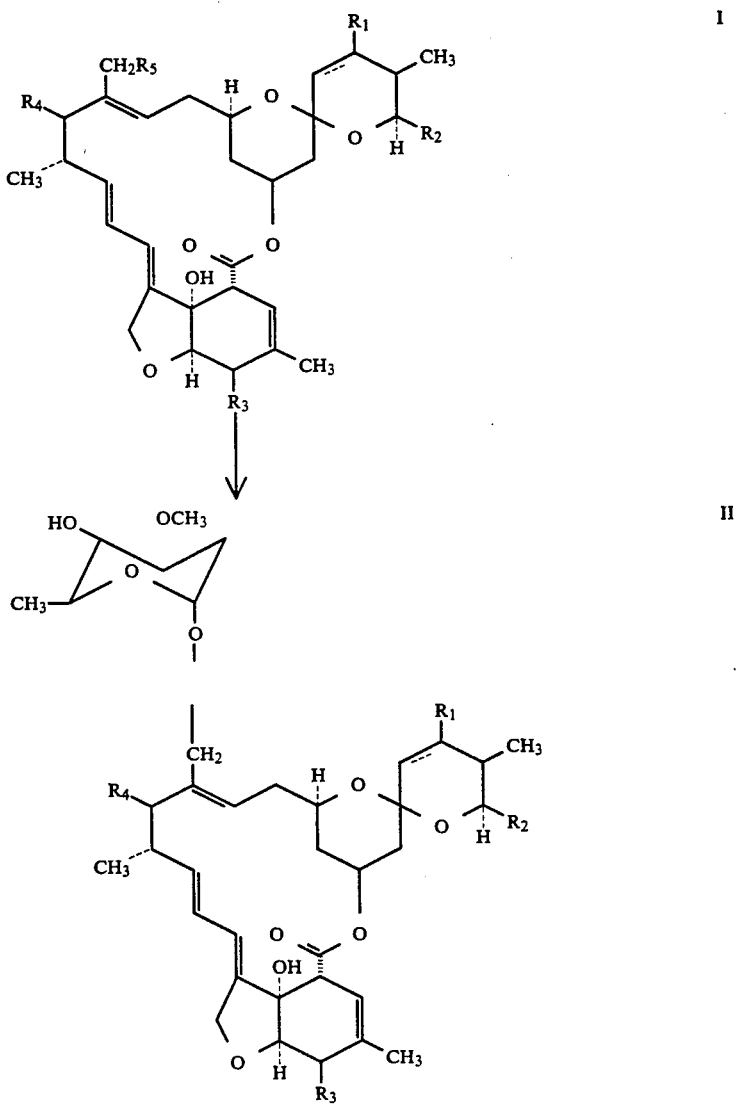

and

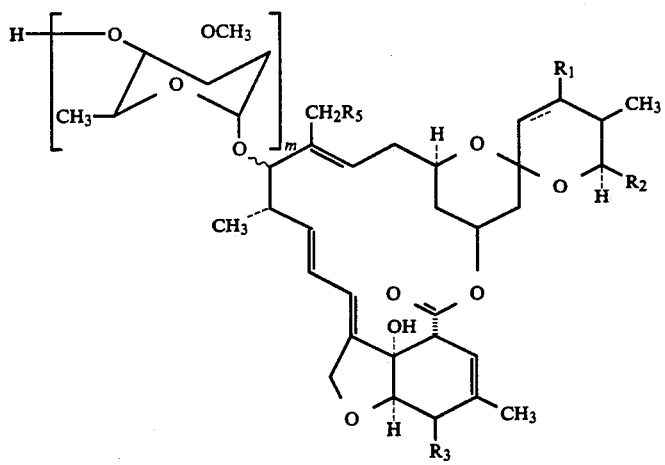

In the above reaction scheme the broken line at the 22,23-position indicates a single or a double bond at the 22,23-position;

$R_1$ is present only when the broken line represents a single bond at the 22,23-position and is hydrogen, hydroxy, oxo, or hydroximino;

$R_2$ is alkyl of 1 to 8 carbon atoms, alkenyl of 2 to 8 carbon atoms or cycloalkyl of 3 to 8 carbon atoms;

$R_3$ is hydroxy, oxo, methoxy or acetoxy; and $R_4$ is hydrogen, hydroxy, or

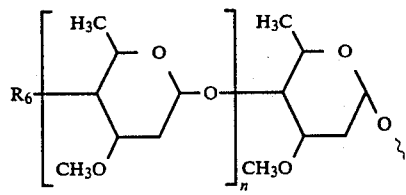

where n is 0 or 1;

m is 1 or 2;

$R_6$ is hydroxy, amino, alkyl of 1 to 8 carbon atoms dialkyl of 1 to 8 carbon atoms or (alkyl of 1 to 8 carbon atoms) (alkanoyl of 1 to 8 carbon atoms)amino; and $R_5$ is hydrogen or hydroxy.

The above compounds of Formulae II and III are active anthelmentic agents.

The instant process is carried out by adding a compound of Formula I to the fermentation broth of *Streptomyces avermitilis* MA 6941 and carrying out the fermentation as described below. The compounds of Formula II are formed when $R_5$ is hydroxy and the compounds of Formula III are formed when $R_5$ is hydrogen and $R_4$ is hydroxy. Also possible are compounds with oleandrose substitution at both the 13- and 14a positions if both $R_4$ and $R_5$ are hydroxy.

The compounds of Formula I are prepared by fermenting a culture of *Streptomyces lavendulae* MA6555m ATCC 14159, in the presence of a avermectin compound with the normal 14-methyl group. The general conditions for the fermentation are similar to those employed for the instant fermentation. Specific examples describing the preparation of such compounds are included in this specification. In addition, certain 14a-hydroxy compounds are prepared synthetically as described in EP144285. The compound of Formula I can be added to the fermentation broth at any time during the fermentation period however it has been found advantageous to add the starting material after allowing the fermentation to proceed for a portion of its term but, to allow the microorganism sufficient time to operate on the starting material, before the fermentation term is complete. Generally, the starting material is added after the fermentation term is at least 10% complete but before it is 75% complete. Preferably the starting material is added when the fermentation has completed from 20% to 50% of its scheduled term.

The starting material is added to the fermentation broth in quantities of from 0.1 to 10 mg per ml of fermentation broth. Preferably the starting material is added in quantities of from 1 to 8 mg per ml. of fermentation broth.

The preferred compounds of the instant invention are realized when in the above structural Formula II:

the broken line at the 22,23-position indicates a 22,23-double bond and $R_1$ is not present;

$R_2$ is isopropyl or sec-butyl;

$R_3$ is hydroxy; and $R_4$ is hydrogen or hydroxy.

The above described strain of *Streptomyces avermitilis* MA 6941, ATCC 55292 is illustrative of a strain which can be employed in the production of the instant compounds. However, the present invention also embraces mutants of the above described microorganism. For example, those mutants which are Obtained by natural selection or those produced by mutating agents including ionizing radiation such as ultraviolet irradiation, or chemical mutagens such as nitrosoguanidine or the like treatments are also included within the ambit of this invention.

The instant compounds are produced during the aerobic fermentation of suitable aqueous nutrient media under conditions described hereinafter, with a non-producing strain of *Streptomyces avermitilis* MA 6941, ATCC 55292. Aqueous media such as those used for the production of many antibiotic substances are suitable for use in this process for the production of this macrocyclic compound. Such nutrient media contain sources of carbon and nitrogen assimilable by the microorganism and generally low levels of inorganic salts. In addition, the fermentation media may contain small amounts of inorganic salts and traces of metals necessary for the growth of the microorganisms, and production of the desired compounds. These are usually present in sufficient concentrations in the complex sources of carbon and nitrogen, which may be used as nutrient sources, but can, of course, be added separately to the medium if desired.

In general, carbohydrates such as sugars, for example dextrose, sucrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 0.5 and 5% by weight of the medium is satisfactory. These carbon sources can be used individually or several such carbon sources may be combined in the same medium.

Various nitrogen sources such as yeast hydrolysates, yeas& autolysates, yeast cells, tomato paste, corn meal, oat flour, soybean meal, casein hydrolysates, yeast extracts, corn steep liquors, distillers solubles, cottonseed meal, meat extract and the like, are readily assimilable by Streptomyces avermitilis MA 6941, ATCC 55292 in the production of the instant compounds. The various sources of nitrogen can be used alone or in combination in amounts ranging from 0.2 to 6% by weight of the medium.

Among the nutrient inorganic salts, which can be incorporated in the culture media are the customary salts capable of yielding sodium, Potassium, magnesium, ammonium, calcium, phosphate, sulfate, chloride, carbonate, and like ions. Also included are trace metals such as cobalt, manganese, and the like.

It should be noted that the media described hereinbelow and in the Examples are merely illustrative of the wide variety of media, which may be employed, and are not intended to be limitative.

The following are Examples of media suitable for growing strains of Streptomyces avermitilis MA 6941, ATCC 55292.

| MEDIUM 1 | |
|---|---|
| Glucose | 5 g |
| Commerical Brown Sugar | 10 g |
| Tryptone | 5 g |
| Yeast Extract | 2.5 g |
| EDTA (ethylene diamine tetracetic acid) | 36 mg |
| betaine | 1.29 g |
| sodium propionate | 0.11 g |
| distilled H$_2$O | 1100 ml |
| pH 7.0–pH 7.2 | |

| MEDIUM 2 | |
|---|---|
| Sucrose | 15 g |
| Peptone | 5.0 g |
| Yeast extract | 2.5 g |
| L-arginine | 0.5 g |
| Distilled H$_2$O | 1000 ml |
| pH 7.0 | |

| MEDIUM 3 | |
|---|---|
| Glucose | 50 g |
| NaCl | 5.0 g |
| (NH$_4$)$_2$SO$_4$ | 2.0 g |
| CaCO$_3$ | 6.0 g |
| propanol | 5 g |
| soya flour | 30 g |
| distilled H$_2$O | 1000 ml |

| MEDIUM 4 | |
|---|---|
| Soluble starch | 15 g |
| Soytone | 20 g |
| CaCl$_2$ | 0.1 g |
| yeast extract | 1.5 g |
| soya oil | 50 ml |
| MOPS (Morpholino propane sulfonic acid) | 10 5 ml |

| MEDIUM 5 | |
|---|---|
| K$_2$HPO$_4$ | 450 mg |
| saccharose | 2.0 g |
| casein | 1.5 g |
| NaCl | 50 mg |
| L-arginine | 15 mg |
| trace element mix A | 1.0 ml |
| distilled water | 1000 ml |
| pH 6.9 | |

| TRACE ELEMENT MIX | |
|---|---|
| Citric Acid | 46.2 mg |
| FeSO$_4$.7H$_2$O | 2.0 ml |
| ZnSO$_4$.7H$_2$O | 1.0 mg |
| MnCl$_2$.4H$_2$O | 0.8 mg |
| CoCl$_2$.6H$_2$O | 0.1 mg |
| MgSO$_4$.7H$_2$O | 50 ml |
| Ascobic acid | 0.12 mg |
| H$_2$O | 160 ml |

| MEDIUM 6 | |
|---|---|
| Cottonseed oil | 5.0 g |
| yeast extract | 0.5 g |
| dextrose | 4.5 g |
| soybean oil | 0.5 ul |
| CaCO$_3$ | 0.6 g |
| Trace element mix | 1.0 ml |
| distilled H$_2$O | 1000 ml |

The fermentations employing Streptomyces avermitilis MA 6941, ATCC 55292 can be conducted at temperatures ranging from about 20° C. to about 40° C. For optimum results, it is most convenient to conduct these fermentations at a temperature in the range of from about 24° C. to about 30°C. Temperatures of about 27°–28° C. are most preferred. The pH of the nutrient medium suitable for producing the instant compounds can vary from about 5.0 to 8.5 with a preferred range of from about 6.0 to 7.5.

Small scale fermentations are conveniently carried out by placing suitable quantities of nutrient medium in a flask employing known sterile techniques, inoculating the flask with either spores Or vegetative cellular growth of Streptomyces avermitilis MA 6941, ATCC 55292, loosely stoppering the flask with cotton and permitting the fermentation to proceed in a constant room temperature of about 30° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of Streptomyces avermitilis MA 6941, ATCC 55292. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 500 RPM and about 50 to 500 liters per minute of air.

The novel compounds of this invention are found both in the aqueous portion and the mycelia of the fermentation medium on termination of the *Streptomyces avermitilis* MA 6941, ATCC 55292 fermentation and may be removed and separated there from as described below.

The separation of the novel compounds from the whole fermentation broth and the recovery of said compounds is carried out by solvent extraction and application of chromatographic fractionations with various chromatographic techniques and solvent systems.

The instant compounds have slight solubility in water, but are soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform, methyl ethyl ketone and the like. Generally several extractions are desirable to achieve maximum recovery. The solvent removes the instant compounds as well as other substances lacking the antiparasitic activity of the instant compounds. If the solvent is a water immiscible one, the layers are separated and the organic solvent is evaporated under reduced pressure. If the solvent is water miscible, it can be extracted with a water immiscible solvent to separate the entrained water. This solvent can then be concentrated under reduced pressure. The residue is placed onto a chromatography column containing preferably, silica gel. The column retains the desired products and some impurities, but lets many of the impurities, particularly the nonpolar impurities, pass through. The column is washed with a moderately polar organic solvent such as methylene chloride, chloride, hexane to further remove impurities, and is then washed with a mixture of methylene chloride, chloroform or hexane and an organic solvent of which acetone, ethyl acetate, methanol, and ethanol and the like are preferred. The solvent is evaporated and the residue further chromatographed using column chromatography, thin layer chromatography, preparative layer chromatography, high pressure liquid chromatography and the like, with silica gel, aluminum oxide, dextran gels and the like, as the chromatographic medium, with various solvents and combinations of solvents as the eluent. Thin layer, high pressure, liquid and preparative layer chromatography may be employed to detect the pressure of, and to isolate the instant compounds. The use of the foregoing techniques as well s other known to those skilled in the art, will afford purified compositions containing the instant compounds. The presence of the desired compounds is determined by analyzing the various chromatographic fractions for biological activity against selected parasites, or physicochemical characteristics. The structures of the instant compounds has been determined by detailed analysis of the various spectral characteristics of the compounds, in particular their nuclear magnetic resonance, mass, ultraviolet and infrared spectra.

The instant compounds are potent endo-and ecto-antiparasitic agents against parasites particularly helminths, ectoparasites, insects, and acarides, infecting man, animals and plants, thus having utility in human and animal health, agriculture and pest control in household and commercial areas.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, fish, buffalo, camels, llamas, reindeer, laboratory animals, furbearing animals, zoo animals and exotic species and poultry. Among the helminths, the group of worms described as nematodes causes widespread and often times serious infection in various species of animals. The most common genera of menatodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Habronema, Druschia, Heterakis, Toxocara, Ascaridia, Oxyuris, Ancylostoma, Uncinaria, Toxascaris and Parascaris. Certain of these, such as Nematodirus, Cooperia, and Oesophagostromum attach primarily the intestinal tract while others, such as Haemonchus and Ostertagia, are more prevalent in the stomach while still other such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs and cats, Nematospiroides, Synphacia, Aspiculuris in rodents, arthropod ectoparasites of animals and birds such as ticks, mites, lice, fleas, blowflies, in sheep *Lucilia* sp., biting insects and such migrating diperous larvae as Hypoderma sp. cattle, Gastrophilus in horses, and Cuterebra sp. in rodents and nuisance flies including blood feeding flies and filth flies.

The instant compounds are also useful against parasites which infect humans. The most common genera of parasites of the gastro-intestinal tract of man are Anyclostoma, Necator, Ascaris, Strongyloides, Trichinella, Capillaria, Trichuris, and Enterobius. Other medically important of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., the housefly *Musca domestica* as well as fleas, house dust mites, termites and ants.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are also highly useful in treating acerage infested with fire ant nests. The compounds are scattered above the infested area in low levels in bait formulations which are broght back to the nest. In addition to a direct-but-slow onset toxic effect on the fire ants, the compound has a long-term effect on the nest by sterilizing the queen which effectively destroys the nest.

The compounds of this invention may be administered in formulations wherein the active compound is intimately admixed with one or more inert ingredients and optionally indlucing one or more additiona active ingredients. The compounds may be used in any composition known to those skilled in the art for administration to humans and animals, for application to plants and for premise and area application to control household pests in either a residential or commercial setting. For application to humans and animals to control internal and external parasites, oral formulations, in solid or liquid or parenteral liquid, implant or depot injection forms may be used. For topical application dip, spray, powder, dust, pour-on, spot-on, jetting fluid, shampoos, collar, tag or harness, may be used. For agricultural premise or area applications, liquid spray, powders, dust, or bait forms may be used. In addition "feed-through" forms may be used to control nuisance flies that feed or breed in animal waste. The compounds are formulated, such as by encapsulation, to lease a residue of active agent in the animal waste which controls filth flies or other arthropod pests.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat. Alternatively, the antiparasitic compounds of this invention may be administered to animals parenterally, for example, by intraruminal, intramuscular, intravascular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, propylene glycol, and aqueous parenteral formulations are also used. The active compound or compounds are dissolved or suspended in the parenteral formulation for administration; such formulations generally contain from 0.0005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting arthropods in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient& of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired antiparasitic result.

In using the compounds of this invention, the individual compounds may be prepared and used in that form. Alternatively, mixtures of the individual compounds may be used, or other active compounds not related to the compounds of this invention.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

PROCEDURES AND EXAMPLES OF PREPARATION OF 14a HYDROXY ARMECTIN/MIBEMYCINS

Culture Conditions

1. Preparation of Frozen Cultures

An L-tube (lyophilized culture) of *Streptomyces lavendulae* (MA6555 ATCC 14159) is aseptically transferred to 250 ml of medium A in 2000 ml baffled erlenmeyer flask and the flask is incubated on a rotary shaker (220 rpm) at 27° C. at 85% humidity for 48 hours. Two ml aliquots of the culture were frozen and stored at $-80°$ C. and served as a source of frozen cultures.

2. Seed Cultures

A vial of frozen culture (2 ml) was used to inoculate a 250 ml baffled erlenmeyer flask containing 50 ml medium A. The flasks were incubated on a rotary shaker (220 ml) at 27° C. at 85% humidity for 24 hours.

3. Transformation Cultures

Five ml of developed seed culture was used to inoculate 50 ml of medium B in a 250 ml erlenmeyer flask; 13-deoxy avermectin $B_1a$(1–5 mg) or 13-deoxy avermectin $B_1b$(0.2–1.0 mg) in DMSO was added at 0 hours. The transformation flasks were incubated for 7 days at 27° C. (220 rpm) at 85% humidity.

| Medium A | |
|---|---|
| Dextrose | 1 g |
| Dextrin | 10 g |
| Beef Extract | 3 g |
| Ardamine pH | 5 g |
| NZ Amine Type E | 5 g |
| $MgSO_4 \cdot 7H_2O$ | .05 g |
| $K_2HPO_4$ | 0.3 g |
| $CaCO_3$ | 0.5 g |
| Distilled $H_2O$ | 1000 ml |
| Medium B | |
| Soluble Starch | 30 g |
| Hycase SF | 2 g |
| Beef Extract | 1 g |
| Corn Steep Liquor | 3 g |
| Morpholinepropanesulfonic acid | 30 g |
| Adjust to pH 7.0 | |

Isolation of 14a-Hydroxy Avermectins

Flasks were extracted with three 50 ml portions of $CH_2Cl_2$. The $CH_2Cl_2$ extracts were combined and concentrated. The hydroxylated products were isolated by HPLC on a Dupont Zorbax ODS columns using $CH_2OH:H_2O$ (85:15, 80:20, or 70:30) as the mobile phase. The structures of the purfied avermectins were determined by NMR and mass spectroscopy.

SPECIFIC EXAMPLES

The following compounds have been prepared by the above procedure:

| Starting material | Product |
|---|---|
| Preparation 1 | |
| 13 deoxy avermectin $B_1a$ aglycone | 13-deoxy-14a-hydroxy avermectin $B_1a$ aglycone |
| Preparation 2 | |
| 13 deoxy avermectin $B_1a$ aglycone | 13$\beta$-hydroxy-14a-hydroxy avermectin $B_1b$ aglycone |
| Preparation 3 | |
| 13 deoxy avermectin $B_1b$ aglycone | 13-deoxy-14a-hydroxy avermectin $B_1b$ aglycone |
| Preparation 4 | |
| 13 deoxy avermectin $B_1b$ aglycone | 13$\beta$-hydroxy-14a-hydroxy avermectin $B_1a$ aglycone |

PROCEDURES AND EXAMPLES OF PREPARATION OF 14a-O-OLEANDROSYL AVERMECTINS/MILBEMYCINS

Culture Conditions

1. Innoculum Preparation

Frozen vegatative mycelia (FVM) of *Streptomyces avermitilis* MA 6941 ATCC 55292 were prepared by innoculating 250 ml seed medium in a 2 liter 3 baffle flask with a lyophilized culture and incubating at 27° C., 85% relative humidity and 200 rpm for 16 hours. The packed cell volume of the culture was 10–15% and the pH 5.7–6.8. Aliquots of the culture were frozen and used as a source of innoculum for future experiments.

Seed Cultures To 25 ml of seed culture in a 250 ml 3 baffle flask, 1.0 ml of FVM was added and the flasks were at 27° C., 85% relative humidity and 200 rpm for 16 hours.

3. Biotransformation and Isolation

To 22.5 ml of biotransformation medium, 1.0 ml of seed culture was added and flasks were incubated at 27° C., 85% relative humidity at 200 rpm for 48 hours. 1.0 mg of 14a-hydroxy avermectin B1a in 0.05 ml dimethylsulfoxide was added and the flasks were incubated for 8 days at 27° C., 85% relative humidity and 220 rpm. Each flask was extracted with 50 ml portions of methylene chloride. The methylene chloride extracts were combined and concentrated. The avermectin monosaccharides were isolated by HPLC on a Dupont Zorbox ODS column using methanol:water (85:15, 80:20, 70:30) as the mobile phase. The structures of the purified avermectins were determined by mass and NMR spectroscopy.

| Seed Medium | |
|---|---|
| Difco yeast extract | 20 g/l |
| Hycase S.F. | 20 g/l |

-continued

| | |
|---|---|
| Dextrose | 20 g/l |
| KNO₃ | 2.0 |
| NaCl | 0.5 |
| MnSO₄.H₂O | .005 |
| ZnSO₄.7H₂O | 0.01 |
| CaCl₂.2H₂O | 0.02 |
| FeSO₄.7H₂O | 0.025 |
| pH = 7.0 | |

| Biotransformation Medium | |
|---|---|
| Peptonized Milk | 17.5 g/l |
| Ardamine pH | 2.7 g/l |
| Dextrose | 75 g/l |
| CuSO₄.5H₂O | 0.00006 g/l |
| ZnSO₄.7H₂O | 0.001 g/l |
| CoCl₂.6H₂O | 0.0001 g/l |
| FeCl₃.6H₂O | 0.003 g/l |
| MgSO₄.7H₂O | 0.5 g/l |
| pH = 7.2 | |

The following compounds have been prepared
13-deoxy-14a-hydroxy avermectin B1a aglycone→13-deoxy-14a-O-oleandrosyloxy avermectin B1a aglycone 13-deoxy-14a-hydroxy avermectin B1b aglycone→13-deoxy-14a-O-oleandrosyloxy avermectin B1b aglycone 13-deoxy-14a-hydroxy-22,23-dihydro avermectin B1a aglycone→13-deoxy-14a-O-oleandrosyloxy-22,23-dihydro avermectin B1a aglycone 13-deoxy-14a-hydroxy-22,23-dihydro avermectin B1b aglycone→13-deoxy-14a-O-oleandrosyloxy-22,23-dihydro avermectin B1b aglycone 13β-14a-hydroxy avermectin B1a aglycone→13β-14a-O-oleandrosyloxy avermectin B1a aglycone 13β-14a-hydroxy avermectin B1b aglycone→13β-14a-O-oleandrosyloxy avermectin B1b aglycone 13β-14a-hydroxy-22,23-dihydro-avermectin B1a aglycone→13β-14a-O-oleandrosyloxy-22,23-dihydro avermectin B1a aglycone 13β-14a-hydroxy-22,23-dihydro-avermectin B1b aglycone→13β-14a-O-oleandrosyloxy-22,23-dihydro avermectin B1b aglycone avermectin B1a/B1b aglycone→avermectin B1a/B1b (disaccharide)

avermectin B2a aglycone→avermectin B2a (disaccharide)

22,23-dihydro-avermectin B1a/B1b aglycone→22,23-dihydro avermectin B1a/B1b (disaccharide)

13β-22,23-dihydro-avermectin B1a/B1b aglycone→13β-22,23-dihydro avermectin B1a/B1b monosaccharide 13β-14a-hydroxy, avermectin B1a aglycone→13β-14a-hydroxy, avermectin B1a monosaccharide 13β-avermectin B1a/B1b aglycone→13β-avermectin B1a/B1b monosaccaride 13β-hydroxy milbemycinα3→13β-O-oleandrosyloxy milbemycinα3

13β-hydroxy milbemycinα4→13β-O-oleandrosyloxy milbemycinα4

13β-hydroxy nemadectin→13β-O-oleandrosyloxy nemadectinα.

What is claimed is:

1. A biologically pure culture of a *Streptomyces avermitilis* MA 6941, ATC 55292.

2. A biologically pure culture of the microorganism *Streptomyces avermitilis* MA 6941, ATCC 55292, which is not capable of producing avermectins and which cannot methylate at the C5 hydroxy and which is capable of preparing compounds having the formula and

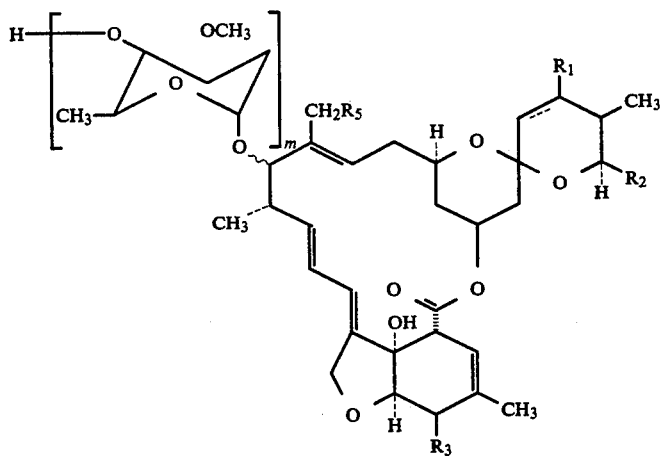

wherein:
R₁ is present only when the broken line represents a single bond at the 22,23-position and is hydrogen, hydroxy, or hydroximino;
R₂ is alkyl of 1 to 8 carbon atoms, alkenyl of 2 to 8 carbon atoms or cycloalkyl of 3 to 8 carbon atoms;
R₃ is hydroxy, methoxy, oxo or acetoxy; and
R⁴ is hydrogen β-hydroxy or

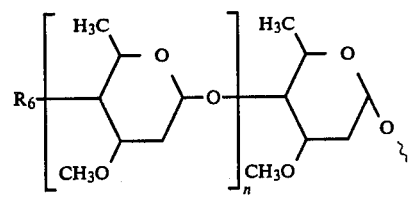

where
n is 0 or 1;
m is 1 or 2;
R₆ is hydroxy, amino, alkyl of 1 to 8 carbon atoms dialkyl of 1 to 8 carbon atoms or (alkyl of 1 to 8 carbon atoms) (alkanoyl of 1 to 8 carbon atoms-)amino; and
R₅ is hydrogen or hydroxy and wherein the fermentation of the microorganism is carried out in an aqueous medium of assimilable sources of carbon, nitrogen and inorganic salts and, as starting material a compound having the formula:

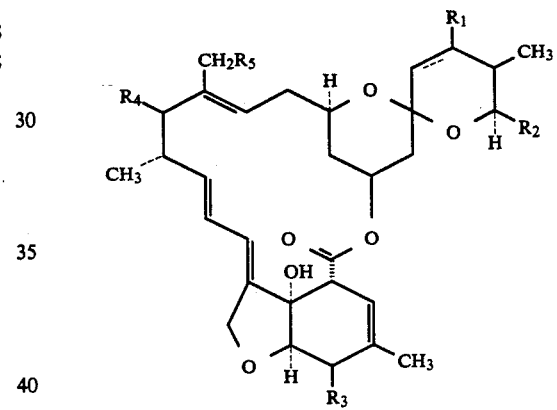

wherein R₁, R₂, R₃, R₄ and R₅ are as defined above provided the starting materials have a 13-hydroxy group or a 14a-hydroxy group, or both, and glycosylation occurs with an oleandrose group only at the 13- or 14a-hydroxy group, or both.

* * * * *